United States Patent
Kaiser et al.

(10) Patent No.: US 10,733,772 B2
(45) Date of Patent: Aug. 4, 2020

(54) METHOD AND PROVIDING UNIT FOR PROVIDING AN OPTIMIZED ENERGY BIN PARAMETER SET FOR PHOTON-COUNTING SPECTRAL COMPUTED TOMOGRAPHY

(71) Applicant: Siemens Healthcare GmbH, Erlangen (DE)

(72) Inventors: Nico Kaiser, Erlangen (DE); Sebastian Schmidt, Weisendorf (DE); Philipp Hoelzer, Bubenreuth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/545,423

(22) Filed: Aug. 20, 2019

(65) Prior Publication Data

US 2020/0066007 A1  Feb. 27, 2020

(30) Foreign Application Priority Data

Aug. 24, 2018 (EP) .................................... 18190617

(51) Int. Cl.
*A61B 5/00* (2006.01)
*G06T 11/00* (2006.01)
(Continued)

(52) U.S. Cl.
CPC ............ *G06T 11/005* (2013.01); *G01T 1/161* (2013.01); *G01T 1/17* (2013.01); *G06N 20/00* (2019.01);
(Continued)

(58) Field of Classification Search
CPC ....... G06T 11/005; G06T 7/11; G06T 7/0012; G06T 2207/10081; G06T 2207/20081;
(Continued)

(56) References Cited

U.S. PATENT DOCUMENTS 9,488,739 B2 * 11/2016 Pelc .................... G01T 1/247
9,672,638 B2 *  6/2017 Rigie ................... G06T 11/005
(Continued)

OTHER PUBLICATIONS

Weidinger, T. et al. "Threshold optimization for efficient contrast imaging with quantum counting CT detectors" SPIE Medical Imaging (2013), Proceedings vol. 8668, Medical Imaging 2013: Physics of Medical Imaging; 86680Q (2013) https://doi.org/10.1117/12.2006518.
(Continued)

*Primary Examiner* — Gregory M Desire
(74) *Attorney, Agent, or Firm* — Harness, Dickey & Pierce, P.L.C.

(57) ABSTRACT

A method is disclosed for providing an optimized energy bin parameter set for photon-counting spectral computed tomography. In one embodiment, the method includes receiving photon-counting spectral computed tomography data related to a plurality of energy bins and an initial energy bin parameter set; and performing iteration steps of a plurality of iteration steps. An input of the first iteration step of the plurality of iteration steps includes the initial energy bin parameter set as an input energy bin parameter set and the input of each further iteration step of the plurality of iteration steps includes an adjusted energy bin parameter set calculated in the preceding iteration step of the plurality of iteration steps as the input energy bin parameter set.

28 Claims, 2 Drawing Sheets

(51) Int. Cl.
  *G06T 7/11* (2017.01)
  *G06T 7/00* (2017.01)
  *G16H 30/40* (2018.01)
  *G06N 20/00* (2019.01)
  *G01T 1/161* (2006.01)
  *G01T 1/17* (2006.01)

(52) U.S. Cl.
  CPC .............. *G06T 7/0012* (2013.01); *G06T 7/11* (2017.01); *G16H 30/40* (2018.01); *G06T 2207/10081* (2013.01); *G06T 2207/20081* (2013.01); *G06T 2210/41* (2013.01); *G06T 2211/424* (2013.01)

(58) Field of Classification Search
  CPC .......... G06T 2210/41; G06T 2211/424; G16H 30/40; G06N 20/00; G01T 1/161; G01T 1/17
  See application file for complete search history.

(56) References Cited

U.S. PATENT DOCUMENTS

| | | | | |
|---|---|---|---|---|
| 9,801,595 | B2 * | 10/2017 | Cao | A61B 6/032 |
| 9,870,628 | B2 * | 1/2018 | Gronberg | A61B 6/5217 |
| 2015/0223766 | A1 * | 8/2015 | Besson | G01T 1/2985 378/5 |
| 2017/0270692 | A1 * | 9/2017 | Gronberg | G06T 11/005 |
| 2018/0038969 | A1 | 2/2018 | McCollough et al. | |

OTHER PUBLICATIONS

Nik, S. J. et al. "Optimal material discrimination using spectral x-ray imaging" Physics in Medicine and Biology, vol. 56, pp. 5696-5983, 2011 // Doi: 10.1088/0031-9155/56/18/012.

Wang, Xiaolan et al. "Optimization of Energy Window Widths in Basis Material Decomposition Using a Multi-window Photon Counting X-ray Detector" 2007 IEEE Nuclear Science Symposium Conference Record, 2007 // DOI: 10.1109/NSSMIC.2007.4436955.

Meng, Bo et al. "Energy Window Optimization for X-ray K-edge Tomographic Imaging" IEEE Transactions on Biomedical Engineering, vol. 63, No. 8, pp. 1623-1630, Aug. 2016 (first published Mar. 2015) DOI: 10.1109/TBME.2015.2413816.

Faby, Sebastian et al. "Performance of today's dual energy CT and future multi energy CT in virtual non-contrast imaging and in iodine quantification: A simulation study" Medical Physics, vol. 42, No. 7, pp. 4349-4366, Jul. 2015 // DOI: 10.1118/1.4922654.

He, Peng et al. "Optimization of K-edge imaging with spectral CT" Medical Physics, vol. 39, No. 11, pp. 6572-6579, Nov. 2012 // DOI: 10.1118/1.4754587.

Choi, Jiyoung et al. "A unified statistical framework for material decomposition using multienergy photon counting x-ray detectors" Medical Physics, vol. 40, No. 9, Sep. 2013 // DOI: 10.1118/1.4817521.

Feng, Chuqing et al. "A multi-energy material decomposition method for spectral CT using neural network" Proceedings of SPIE, Proceedings vol. 10573, Medical Imaging 2018: Physics of Medical Imaging; 105734J (2018) // https://doi.org/10.1117/12.2294611.

NPL: Extended European Search Report for EP Application No. 18190617, dated Jan. 28, 2019.

\* cited by examiner

METHOD AND PROVIDING UNIT FOR PROVIDING AN OPTIMIZED ENERGY BIN PARAMETER SET FOR PHOTON-COUNTING SPECTRAL COMPUTED TOMOGRAPHY

PRIORITY STATEMENT

The present application hereby claims priority under 35 U.S.C. § 119 to European patent application number EP 18190617.3 filed Aug. 24, 2018, the entire contents of which are hereby incorporated herein by reference.

FIELD

At least one embodiment of the invention generally relates to a method for providing an optimized energy bin parameter set for photon-counting spectral computed tomography. Other embodiments of the invention generally relate to a method for providing a medical image and to a method for providing a segmentation of an anatomical structure. A further embodiment of the invention generally relates to a training method for training a machine learning algorithm for providing an optimized energy bin parameter set for photon-counting spectral computed tomography. Further embodiments of the invention generally relate to a providing unit for providing an optimized energy bin parameter set for photon-counting spectral computed tomography, a computer program product, a computer-readable medium and a computed tomography device.

BACKGROUND

Photon-counting detectors for computed tomography enable the generation of spectrally resolved computed tomography medical image data. A photon-counting detector can be configured to acquire x-ray projection data in a plurality on energy bins. For example, four energy bins can be used to cover the whole range of energies of the acquired x-ray projection data. The photon-counting spectral computed tomography data related to the plurality of energy bins can be used to calculate blended images, material decompositions and/or virtual mono-energetic images.

The window parameters of the energy bins may be pre-defined before the start of the acquisition of the x-ray projection data. In a basic approach, the same pre-defined window parameters of the energy bins are used for different kinds of computed tomography applications, without adaption to the specific structure and/or tissue under examination. To improve the quality of the acquired photon-counting spectral computed tomography data, the window parameters of the energy bins may be adapted with regard to the specific computed tomography application. Various methods for providing optimized window parameters of the energy bins have been proposed (see documents [1]-[5] in the Bibliography at the end of the specification).

SUMMARY

The inventors have discovered that an underlying technical problem was a need to facilitate an improved optimization of an energy bin parameter set for photon-counting spectral computed tomography. This problem is solved by the method and/or the providing unit of at least one embodiment. The claims are related to further embodiments of the invention.

In one embodiment of the invention is directed to a method for providing an optimized energy bin parameter set for photon-counting spectral computed tomography, the method comprising:

receiving photon-counting spectral computed tomography data related to a plurality of energy bins and an initial energy bin parameter set;

performing a plurality of iteration steps,
wherein an input of a first iteration step of the plurality of iteration steps comprises the initial energy bin parameter set as an input energy bin parameter set, and
wherein an input of each further iteration step of the plurality of iteration steps comprises an adjusted energy bin parameter set calculated in a preceding iteration step of the plurality of iteration steps as the input energy bin parameter set; and providing the optimized energy bin parameter set based on the adjusted energy bin parameter set calculated in a last iteration step of the plurality of iteration steps,
and wherein each iteration step of the plurality of iteration steps comprises:
a) calculating medical image data by applying at least one reconstruction algorithm onto the photon-counting spectral computed tomography data and the input energy bin parameter set,
b) calculating segmentation data related to an anatomical structure in the medical image data by applying at least one segmentation algorithm onto the medical image data,
c) calculating evaluation data by applying an evaluation algorithm onto the segmentation data, and
d) calculating the adjusted energy bin parameter set by applying an optimization algorithm onto the evaluation data and the input energy bin parameter set.

In another embodiment, the invention relates to a method for providing a segmentation of an anatomical structure, the method comprising:

performing the method for providing an optimized energy bin parameter set for photon-counting spectral computed tomography according to one or more of the disclosed embodiments, thereby obtaining an optimized energy bin parameter set, calculating medical image data by applying at least one reconstruction algorithm onto the photon-counting spectral computed tomography data and the optimized energy bin parameter set, calculating the segmentation of the anatomical structure in the medical image data by applying at least one segmentation algorithm onto the medical image data, and providing the segmentation of the anatomical structure.

In a further embodiment, the invention relates to a training method for training a machine learning algorithm for providing an optimized energy bin parameter set for photon-counting spectral computed tomography, the method comprising:

receiving a plurality of photon-counting spectral computed tomography data sets and an initial energy bin parameter set, for each photon-counting spectral computed tomography data set of the plurality of photon-counting spectral computed tomography data sets, performing the method for providing an optimized energy bin parameter set for photon-counting spectral computed tomography according to one or more of the disclosed embodiments, thereby obtaining, for each photon-counting spectral computed tomography data set, a corresponding optimized energy bin parameter set, generating a plurality of training pairs, each training pair of the plurality of training pairs comprising one photon-counting spectral computed tomography data set of the plurality of photon-counting spectral computed tomography data sets and the corresponding optimized energy bin parameter set, and training the machine learning algorithm based on the plurality of training pairs, thereby obtaining a trained machine learning algorithm for providing an optimized energy bin parameter set for photon-counting spectral computed tomography.

In a further embodiment, the invention relates to a providing unit for providing an optimized energy bin parameter set for photon-counting spectral computed tomography, the providing unit comprising:

a receiving unit, configured for receiving photon-counting spectral computed tomography data related to a plurality of energy bins and an initial energy bin parameter set, an iteration unit, configured for performing iteration steps of a plurality of iteration steps,
  wherein the input of the first iteration step of the plurality of iteration steps comprises the initial energy bin parameter set as an input energy bin parameter set,
  wherein the input of each further iteration step of the plurality of iteration steps comprises an adjusted energy bin parameter set calculated in the preceding iteration step of the plurality of iteration steps as the input energy bin parameter set, and an energy bin parameter set providing interface, configured for providing the optimized energy bin parameter set based on the adjusted energy bin parameter set calculated in the last iteration step of the plurality of iteration steps,
  wherein the iteration unit comprises the following calculation units:
    a) a medical image calculation unit, configured for calculating medical image data by applying at least one reconstruction algorithm onto the photon-counting spectral computed tomography data and the input energy bin parameter set,
    b) a segmentation data calculation unit, configured for calculating segmentation data related to an anatomical structure in the medical image data by applying at least one segmentation algorithm onto the medical image data,
    c) an evaluation data calculation unit, configured for calculating evaluation data by applying an evaluation algorithm onto the segmentation data, and
    d) an optimization calculation unit calculating the adjusted energy bin parameter set by applying an optimization algorithm onto the evaluation data and the input energy bin parameter set.

In a further embodiment, the invention relates to a computer program product comprising program elements which induce a providing unit to carry out the steps of the method according to one or more of the disclosed embodiments, when the program elements are loaded into a memory of the providing unit.

In a further embodiment, the invention relates to a computer-readable medium on which program elements are stored that can be read and executed by a providing unit, in order to perform the steps of the method according to one or more of the disclosed embodiments, when the program elements are executed by the providing unit.

In a further embodiment, the invention relates to a computed tomography device, comprising a providing unit for providing an optimized energy bin parameter set for photon-counting spectral computed tomography according to one or more of the disclosed embodiments.

In a further embodiment, the invention relates to a computed tomography device, comprising:

a detector, configured for acquiring photon-counting spectral computed tomography data related to a plurality of energy bins, and a medical image calculation unit, configured for calculating a medical image by applying a reconstruction algorithm onto the photon-counting spectral computed tomography data and the optimized energy bin parameter set.

In another embodiment, the computed tomography device comprises a processor, configured for applying a trained machine learning algorithm to the photon-counting spectral computed tomography data, thereby obtaining an optimized energy bin parameter set, wherein the trained machine learning algorithm has been trained by the training method for training a machine learning algorithm for providing an optimized energy bin parameter set for photon-counting spectral computed tomography.

BRIEF DESCRIPTION OF THE DRAWINGS

The invention will be illustrated below with reference to the accompanying figures using example embodiments. The illustration in the figures is schematic and highly simplified and not necessarily to scale.

DETAILED DESCRIPTION OF THE EXAMPLE EMBODIMENTS

Figure 1:
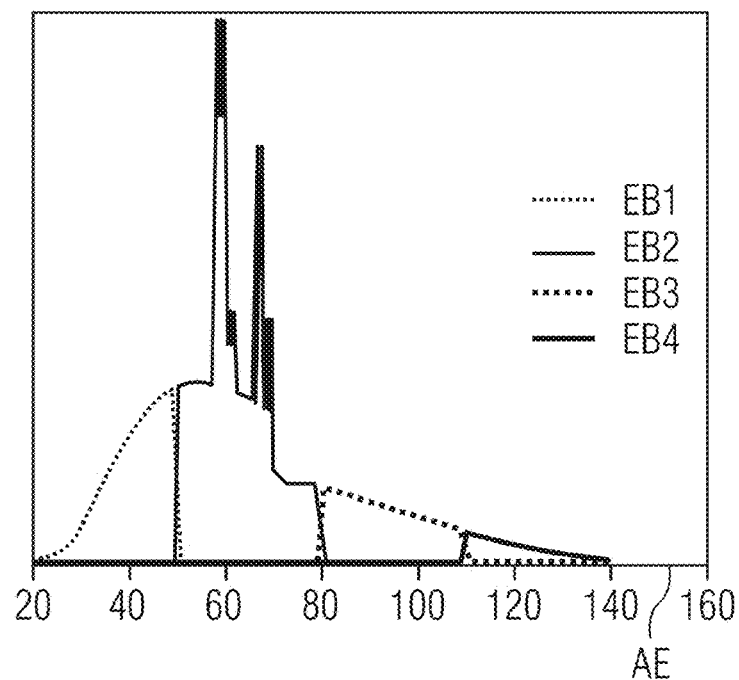
FIG. 1 shows an x-ray spectrum in relation to a plurality of energy bins of a photon counting detector.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In one embodiment of the invention is directed to a method for providing an optimized energy bin parameter set for photon-counting spectral computed tomography, the method comprising:

receiving photon-counting spectral computed tomography data related to a plurality of energy bins and an initial energy bin parameter set, performing iteration steps of a plurality of iteration steps, wherein the input of the first iteration step of the plurality of iteration steps comprises the initial energy bin parameter set as an input energy bin parameter set, wherein the input of each further iteration step of the plurality of iteration steps comprises an adjusted energy bin parameter set calculated in the preceding iteration step of the plurality of iteration steps as the input energy bin parameter set, and providing the optimized energy bin parameter set based on the adjusted energy bin parameter set calculated in the last iteration step of the plurality of iteration steps, wherein each iteration step of the plurality of iteration steps comprises:

a) calculating medical image data by applying at least one reconstruction algorithm onto the photon-counting spectral computed tomography data and the input energy bin parameter set, b) calculating segmentation data related to an anatomical structure in the medical image data by applying at least one segmentation algorithm onto the medical image data, c) calculating evaluation data by applying an evaluation algorithm onto the segmentation data, and d) calculating the adjusted energy bin parameter set by applying an optimization algorithm onto the evaluation data and the input energy bin parameter set.

In another embodiment, the optimized energy bin parameter set comprises a plurality of weighting parameters, wherein the at least one reconstruction algorithm is configured for weighting subsets of the photon-counting spectral computed tomography data relative to each other based on the weighting parameters.

In another embodiment, the segmentation algorithm is a trained deep learning based semantic segmentation algorithm.

In another embodiment, the evaluation algorithm is a trained deep learning based evaluation algorithm.

In another embodiment, each iteration step of the plurality of iteration steps further comprises a step of determining, whether a termination criterion is fulfilled based on the evaluation data.

In another embodiment, the optimization algorithm is an iterative optimization algorithm and/or an evolutionary optimization algorithm.

In another embodiment, the invention relates to a method for providing a medical image, the method comprising:

performing the method for providing an optimized energy bin parameter set for photon-counting spectral computed tomography according to one or more of the disclosed embodiments, thereby obtaining an optimized energy bin parameter set, calculating the medical image by applying a reconstruction algorithm onto the photon-counting spectral computed tomography data and the optimized energy bin parameter set, and providing the medical image.

In another embodiment, the invention relates to a method for providing a segmentation of an anatomical structure, the method comprising:

performing the method for providing an optimized energy bin parameter set for photon-counting spectral computed tomography according to one or more of the disclosed embodiments, thereby obtaining an optimized energy bin parameter set, calculating medical image data by applying at least one reconstruction algorithm onto the photon-counting spectral computed tomography data and the optimized energy bin parameter set, calculating the segmentation of the anatomical structure in the medical image data by applying at least one segmentation algorithm onto the medical image data, and providing the segmentation of the anatomical structure.

In a further embodiment, the invention relates to a training method for training a machine learning algorithm for providing an optimized energy bin parameter set for photon-counting spectral computed tomography, the method comprising:

receiving a plurality of photon-counting spectral computed tomography data sets and an initial energy bin parameter set, for each photon-counting spectral computed tomography data set of the plurality of photon-counting spectral computed tomography data sets, performing the method for providing an optimized energy bin parameter set for photon-counting spectral computed tomography according to one or more of the disclosed embodiments, thereby obtaining, for each photon-counting spectral computed tomography data set, a corresponding optimized energy bin parameter set, generating a plurality of training pairs, each training pair of the plurality of training pairs comprising one photon-counting spectral computed tomography data set of the plurality of photon-counting spectral computed tomography data sets and the corresponding optimized energy bin parameter set, and training the machine learning algorithm based on the plurality of training pairs, thereby obtaining a trained machine learning algorithm for providing an optimized energy bin parameter set for photon-counting spectral computed tomography.

In a further embodiment, the invention relates to a providing unit for providing an optimized energy bin parameter set for photon-counting spectral computed tomography, the providing unit comprising:

a receiving unit, configured for receiving photon-counting spectral computed tomography data related to a plurality of energy bins and an initial energy bin parameter set, an iteration unit, configured for performing iteration steps of a plurality of iteration steps, wherein the input of the first iteration step of the plurality of iteration steps comprises the initial energy bin parameter set as an input energy bin parameter set, wherein the input of each further iteration step of the plurality of iteration steps comprises an adjusted energy bin parameter set calculated in the preceding iteration step of the plurality of iteration steps as the input energy bin parameter set, and an energy bin parameter set providing interface, configured for providing the optimized energy bin parameter set based on the adjusted energy bin parameter set calculated in the last iteration step of the plurality of iteration steps, wherein the iteration unit comprises the following calculation units:

a) a medical image calculation unit, configured for calculating medical image data by applying at least one reconstruction algorithm onto the photon-counting spectral computed tomography data and the input energy bin parameter set, b) a segmentation data calculation unit, configured for calculating segmentation data related to an anatomical structure in the medical image data by applying at least one segmentation algorithm onto the medical image data, c) an evaluation data calculation unit, configured for calculating evaluation data by applying an evaluation algorithm onto the segmentation data, and d) an optimization calculation unit calculating the adjusted energy bin parameter set by applying an optimization algorithm onto the evaluation data and the input energy bin parameter set.

In another embodiment, the providing unit is configured to implement the method for providing an optimized energy bin parameter set for photon-counting spectral computed tomography according to one or more of the disclosed embodiments.

In another embodiment, the providing unit further comprises a medical image providing interface, configured for providing a medical image, wherein the providing unit is further configured to implement the method for providing a medical image according to one or more of the disclosed embodiments.

In another embodiment, the providing unit further comprises a segmentation providing interface, configured for providing a segmentation of an anatomical structure, wherein the providing unit is further configured to implement the method for providing a segmentation of an anatomical structure according to one or more of the disclosed embodiments.

In a further embodiment, the invention relates to a computer program product comprising program elements which induce a providing unit to carry out the steps of the method according to one or more of the disclosed embodiments, when the program elements are loaded into a memory of the providing unit.

In a further embodiment, the invention relates to a computer-readable medium on which program elements are stored that can be read and executed by a providing unit, in order to perform the steps of the method according to one or more of the disclosed embodiments, when the program elements are executed by the providing unit.

In a further embodiment, the invention relates to a computed tomography device, comprising a providing unit for providing an optimized energy bin parameter set for photon-counting spectral computed tomography according to one or more of the disclosed embodiments.

In a further embodiment, the invention relates to a computed tomography device, comprising:

a detector, configured for acquiring photon-counting spectral computed tomography data related to a plurality of energy bins, and a medical image calculation unit, configured for calculating a medical image by applying a reconstruction algorithm onto the photon-counting spectral computed tomography data and the optimized energy bin parameter set.

In another embodiment, the computed tomography device comprises a processor, configured for applying a trained machine learning algorithm to the photon-counting spectral computed tomography data, thereby obtaining an optimized energy bin parameter set, wherein the trained machine learning algorithm has been trained by the training method for training a machine learning algorithm for providing an optimized energy bin parameter set for photon-counting spectral computed tomography.

The photon-counting spectral computed tomography data can comprise a plurality of x-ray projection data sets. Each x-ray projection data set of the plurality of x-ray projection data sets can form a subset of the photon-counting spectral computed tomography data and/or can be assigned to a corresponding energy bin of the plurality of energy bins. An x-ray projection data set assigned to a given energy bin comprises attenuation values of photons of an energy that is comprised in the given energy bin.

An energy bin parameter set may comprise a plurality of weighting parameters, in particular at least one weighting parameter for each energy bin of the plurality of energy bins. The weighting parameters determine the weighting of the x-ray projection data of different energy bins relative to each other by the at least one reconstruction algorithm. Different weighting parameters can be assigned to a given energy bin for use by different reconstruction algorithms. The weighting parameters can determine, for example, whether x-ray projection data related to photons of higher energy will contribute to the reconstructed medical image with a higher weight than x-ray projection data related to photons of lower energy or vice versa.

An energy bin parameter set may comprise a plurality of window parameters, in particular window parameters of different kinds. A window parameter may be, for example, a total amount of energy bins in the plurality of energy bins and/or in an amended plurality of energy bins. A window parameter may be, for example, an energy window width and/or an energy window position and/or one or more threshold values for each energy bin of the plurality of energy bins.

Optimized window parameters of the energy bins can be used, for example, to modify the photon-counting spectral computed tomography data, in particular re-assigning x-ray projection data to different energy bins, and/or to acquire further photon-counting spectral computed tomography data related to the amended plurality of energy bins.

Basically, any initial energy bin parameter set can be used. For example, a pre-defined energy bin parameter set or an energy bin parameter set know from a previous similar computed tomography examination can be used.

The medical image data can comprise one or more medical images of the same kind or of different kinds. Kinds of medical images are, for example, blended images, in particular linear blended images or non-linear blended images, virtual non-contrast images, virtual mono-energetic images and material decomposition images, in particular material-density images.

Basically, any segmentation algorithm may be used. For example, a trained semantic segmentation algorithm, in particular based on a convolutional neural network, can be used as the segmentation algorithm. The trained semantic segmentation algorithm can be applied onto medical image data comprising a plurality of images, in particular a plurality of images of different kinds. The anatomical structure can be, for example, an organ or a part of an organ, in particular of a human body. The anatomical structure can comprise, for example, soft tissue.

The evaluation data may comprise a measure indicative of the quality of the segmentation data. Under otherwise identical conditions, for a given tissue, the quality of the segmentation data would be optimal, if the energy bin parameter set is optimal with respect to the given tissue. In reverse, if it is indicated by the evaluation data, that segmentation data with optimal quality have been obtained for a given tissue, the energy bin parameter set that was used for the calculation of the medical image data underlying the segmentation can be regarded as the optimal one with respect to the given tissue.

The evaluation algorithm can be a trained evaluation algorithm, in particular a trained evaluation algorithm based on a convolutional neural network. For example, a trained evaluation algorithm can be used that has learned how a segmentation of an anatomical structure can look like. To some extent, the trained evaluation algorithm has a similar role like the adversarial/discriminative network of a generative adversarial network. Therefore, the method allows the utilization of knowledge about the anatomical structure of interest, in particular in form of the trained evaluation algorithm.

The evaluation algorithm can be trained, for example, based on manually annotated training data comprising computed tomography data and/or magnetic resonance imaging data and/or synthetic computed tomography data generated from magnetic resonance imaging data. Magnetic resonance imaging data has the advantage of an improved soft tissue contrast.

According to one embodiment, the number of iteration steps in the plurality of iteration steps may be pre-defined. According to another embodiment, the number of iteration steps in the plurality of iteration steps is determined based on a termination criterion. For example, the method can further comprise a step of determining whether a termination criterion is fulfilled based on the evaluation data. The determining whether a termination criterion is fulfilled based on the evaluation data may comprise comparing one or more evaluation values comprised in the evaluation data to corresponding threshold values of the termination criterion.

The termination criterion may be defined in way, that it can only be fulfilled by evaluation data that have been calculated based on segmentation data the quality of which is optimal or close to optimal. The iteration step, during which the adjusted energy bin parameter set has been calculated, that, if used together with the photon-counting spectral computed tomography data as an input for the reconstruction algorithm, yields medical image data, that, if used as an input for the segmentation algorithm, yields segmentation data, that, if used as an input for the evaluation algorithm, yields evaluation data that fulfill the termination criterion, can be regarded as the last iteration step of the plurality of iteration steps.

The optimization algorithm may use data, for example evaluation data and/or adjusted energy bin parameter sets that already have been calculated during one or more earlier iteration steps of the plurality of iteration steps as further input. The optimization algorithm can be an iterative optimization algorithm and/or an evolutionary optimization algorithm. The optimization algorithm can be based, for example, on gradient descent and/or on Maximum-Likelihood Expectation-Maximization (MLEM).

The method can provide an optimal energy bin parameter set with respect to a given anatomical structure, such as an organ, and/or a tissue. In particular, it is not necessary to provide a topogram data that was acquired before the photon-counting spectral computed tomography data in order to obtain the optimal energy bin parameter set.

The optimal energy bin parameter set can be used together with the photon-counting spectral computed tomography data as an input for the reconstruction algorithm to calculate medical images, for example, blended images, virtual non-contrast images, virtual mono-energetic images and material decomposition images. A medical image calculated based on the optimal energy bin parameter set is expected to have improved contrast, because a clear delineation of the anatomical structures comprised in the medical image is a prerequisite for high quality segmentation. Furthermore, the method can provide optimal segmentation data of an anatomical structure based on photon-counting spectral computed tomography data. The optimal segmentation can be obtained by applying the segmentation algorithm onto the medical image data that was calculated based on the photon-counting spectral computed tomography and the optimal energy bin parameter set.

The proposed method can provide improved medical images and/or improved segmentation, especially of soft tissue anatomical structures, like brain or liver. The proposed method allows the optimal utilization of spectral information. Furthermore, it is not necessary to provide annotated spectral computed tomography training data in order to perform the method.

Based on the trained machine learning algorithm, an optimized energy bin parameter set can be provided for given photon-counting spectral computed tomography data without performing the iteration steps explicitly for the given photon-counting spectral computed tomography data. In particular, the machine learning algorithm can be trained based on a large amount of computed tomography data sets and corresponding optimized energy bin parameter sets that are related to the same structure and/or tissue, for example brain. Then the trained machine learning algorithm is particularly suitable for providing an optimized energy bin parameter set with respect to that structure and/or tissue. The machine learning algorithm can be based, for example, on a convolutional neural network.

Any of the units or interfaces mentioned herein can be embodied in form of hardware and/or software. In particular, an interface can be embodied in form of at least one of a PCI-Bus, a USB or a Firewire. In particular, a unit can comprise hardware elements and/or software elements, for example a microprocessor, a field programmable gate array (an acronym is "FPGA") or an application specific integrated circuit (an acronym is "ASIC"). A computer-readable medium can be embodied as non-permanent main memory (e.g. random access memory) or as permanent mass storage (e.g. hard disk, USB stick, SD card, solid state disk).

The providing unit can be embodied as a data processing system or as a part of a data processing system. The data processing system can, for example, comprise at least one of a cloud-computing system, a distributed computing system, a computer network, a computer, a tablet computer, a smartphone or the like. The data processing system can comprise hardware and/or software. The hardware can be, for example, a processor system, a memory system and combinations thereof. The hardware can be configurable by the software and/or be operable by the software. Calculations for performing steps of a method and/or for training an algorithm may be carried out in a processor. Data, in particular, an optimized energy bin parameter set, a medical image or a segmentation, can be provided, for example, by transmitting a signal that carries the data and/or by writing the data into a computer-readable medium and/or by displaying the data on a display.

The computer program product can be, for example, a computer program or comprise another element apart from the computer program. This other element can be hardware, for example a memory device, on which the computer program is stored, a hardware key for using the computer program and the like, and/or software, for example, a documentation or a software key for using the computer program.

Wherever not already described explicitly, individual embodiments, or their individual embodiments and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

Any of the algorithms mentioned herein can be based on one or more of the following architectures: convolutional neural networks, deep belief networks, deep residual learning, deep reinforcement learning, recurrent neural networks, Siamese networks, generative adversarial networks or autoencoders. In particular, the trained machine learning algorithm for providing an optimized energy bin parameter set for photon-counting spectral computed tomography can be embodied as a deep learning algorithm and/or as a convolutional neural network.

Reference is made to the fact that the described methods and the described units are merely preferred example embodiments of the invention and that the invention can be varied by a person skilled in the art, without departing from the scope of the invention as it is specified by the claims.

FIG. 1 shows an x-ray spectrum in relation to a plurality of energy bins of a photon counting detector. In the illustrated in FIG. 1, the plurality of energy bins consists of four energy bins. The axis AE shows values for photon energies in keV. Each of the lines EB1, EB2, EB3 and EB4 marks a part of the x-ray spectrum that is related to one of the four energy bins. The use of four energy bins allows a good signal-to-noise ratio at a reasonable computational effort.

Attenuation values of photons from the part of the x-ray spectrum that is marked with line EB1 are assigned to the first energy bin of the four energy bins. Attenuation values of photons from the part of the x-ray spectrum that is marked with line EB2 are assigned to the second energy bin of the four energy bins. Attenuation values of photons from the part of the x-ray spectrum that is marked with line EB3 are assigned to the third energy bin of the four energy bins. Attenuation values of photons from the part of the x-ray spectrum that is marked with line EB4 are assigned to the fourth energy bin of the four energy bins.

Figure 2:
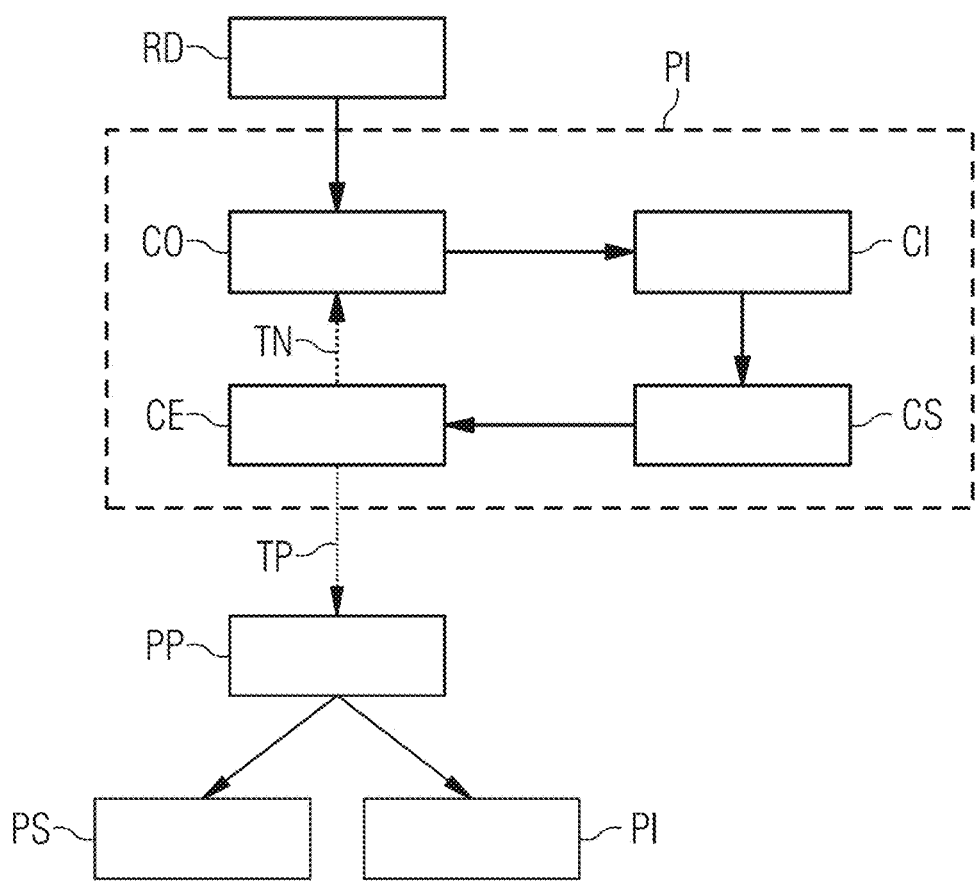
FIG. 2 shows a diagram illustrating a method for providing an optimized energy bin parameter set for photon-counting spectral computed tomography.

FIG. 2 shows a diagram illustrating a method for providing an optimized energy bin parameter set for photon-counting spectral computed tomography, the method comprising:

receiving RD photon-counting spectral computed tomography data related to a plurality of energy bins and an initial energy bin parameter set, and performing PI iteration steps of a plurality of iteration steps, wherein the input of the first iteration step of the plurality of iteration steps comprises the initial energy bin parameter set as an input energy bin parameter set, wherein the input of each further iteration step of the plurality of iteration steps comprises an adjusted energy bin parameter set calculated in the preceding iteration step of the plurality of iteration steps as the input energy bin parameter set, providing PP the optimized energy bin parameter set based on the adjusted energy bin parameter set calculated in the last iteration step of the plurality of iteration steps, wherein each iteration step of the plurality of iteration steps comprises the following:
  a) calculating CI medical image data by applying at least one reconstruction algorithm onto the photon-counting spectral computed tomography data and the input energy bin parameter set,
  b) calculating CS segmentation data related to an anatomical structure in the medical image data by applying at least one segmentation algorithm onto the medical image data,
  c) calculating CE evaluation data by applying an evaluation algorithm onto the segmentation data, and
  d) calculating CO the adjusted energy bin parameter set by applying an optimization algorithm onto the evaluation data and the input energy bin parameter set.

Each iteration step of the plurality of iteration steps further comprises a step of determining, whether a termination criterion is fulfilled based on the evaluation data. If the termination criterion is not-fulfilled, the iteration is continued TN. If the termination criterion is fulfilled, the iteration is terminated TP.

In step PI, a medical image is provided that has been calculated by applying a reconstruction algorithm onto the photon-counting spectral computed tomography data and the optimized energy bin parameter set In step PS, a segmentation of the anatomical structure is provided that has been calculated by applying at least one segmentation algorithm onto the medical image data that has been calculated by applying at least one reconstruction algorithm onto the photon-counting spectral computed tomography data and the optimized energy bin parameter set.

Figure 3:
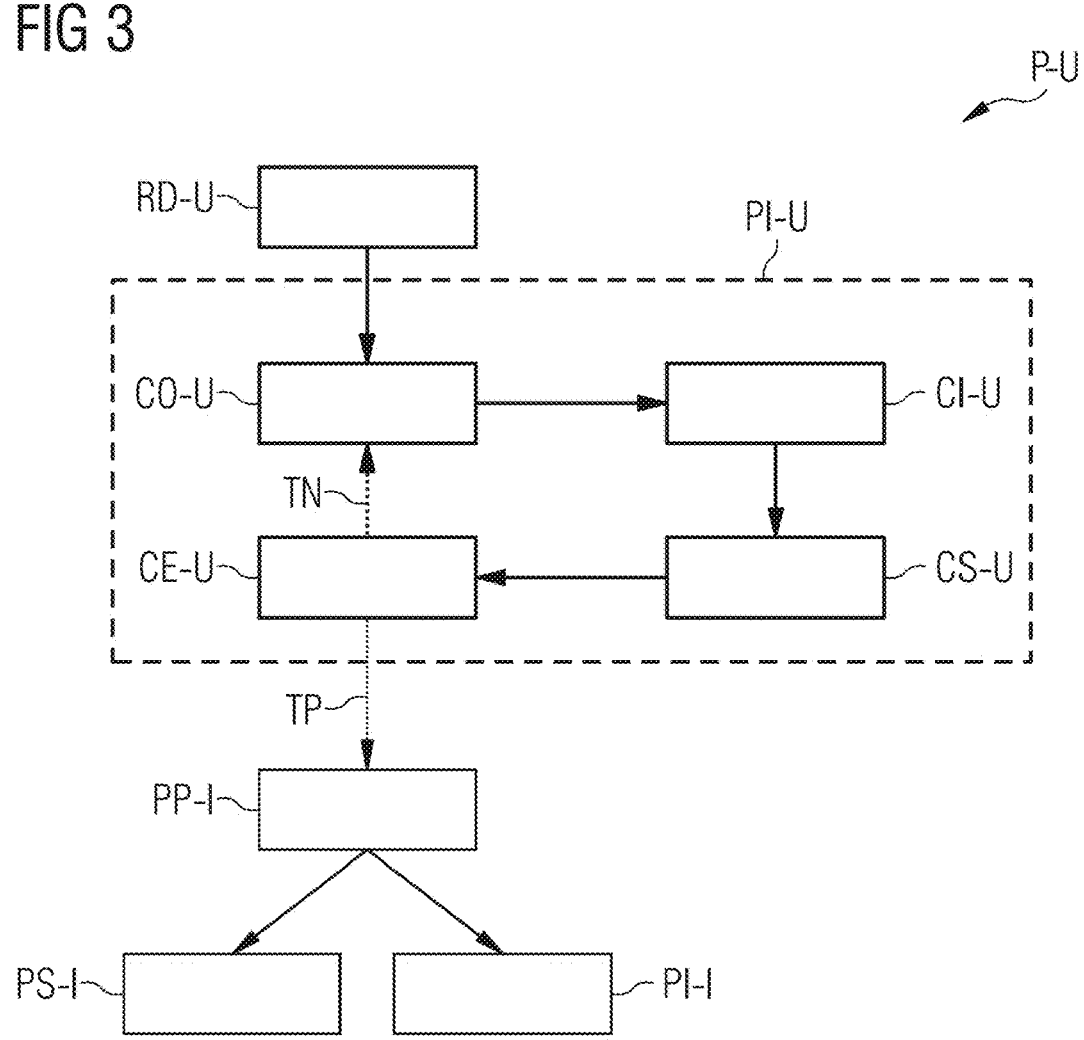
FIG. 3 shows a providing unit for providing an optimized energy bin parameter set for photon-counting spectral computed tomography.

FIG. 3 shows a providing unit P-U for providing an optimized energy bin parameter set for photon-counting spectral computed tomography, the providing unit comprising:

a receiving unit RD-U, configured for receiving photon-counting spectral computed tomography data related to a plurality of energy bins and an initial energy bin parameter set, an iteration unit PI-U, configured for performing iteration steps of a plurality of iteration steps, wherein the input of the first iteration step of the plurality of iteration steps comprises the initial energy bin parameter set as an input energy bin parameter set, wherein the input of each further iteration step of the plurality of iteration steps comprises an adjusted energy bin parameter set calculated in the preceding iteration step of the plurality of iteration steps as the input energy bin parameter set, an energy bin parameter set providing interface PP-I, configured for providing the optimized energy bin parameter set based on the adjusted energy bin parameter set calculated in the last iteration step of the plurality of iteration steps, wherein the iteration unit PI-U comprises the following calculation units:
  a) a medical image calculation unit CI-U, configured for calculating medical image data by applying at least one reconstruction algorithm onto the photon-counting spectral computed tomography data and the input energy bin parameter set,
  b) a segmentation data calculation unit CS-U, configured for calculating segmentation data related to an anatomical structure in the medical image data by applying at least one segmentation algorithm onto the medical image data,
  c) an evaluation data calculation unit CE-U, configured for calculating evaluation data by applying an evaluation algorithm onto the segmentation data, and
  d) an optimization calculation unit CO-U calculating the adjusted energy bin parameter set by applying an optimization algorithm onto the evaluation data and the input energy bin parameter set.

The providing unit P-U is configured to implement the method illustrated in FIG. 2. The providing unit P-U further comprises a medical image providing interface PI-I, configured for providing a medical image, and a segmentation providing interface PS-I, configured for providing a segmentation of an anatomical structure.

The providing unit P-U further comprises a determining unit, configured for determining whether a termination criterion is fulfilled based on the evaluation data. If the termination criterion is not-fulfilled, the iteration is continued TN. If the termination criterion is fulfilled, the iteration is terminated TP.

Figure 4:
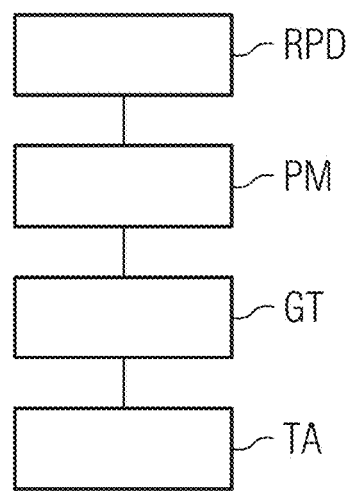
FIG. 4 shows a diagram illustrating a training method for training a machine learning algorithm for providing an optimized energy bin parameter set for photon-counting spectral computed tomography.

FIG. 4 shows a diagram illustrating a training method for training a machine learning algorithm for providing an optimized energy bin parameter set for photon-counting spectral computed tomography, the method comprising:

receiving RPD a plurality of photon-counting spectral computed tomography data sets and an initial energy bin parameter set, for each photon-counting spectral computed tomography data set of the plurality of photon-counting spectral computed tomography data sets, performing PM the method for providing an optimized energy bin parameter set for photon-counting spectral computed tomography according to one or more of the disclosed embodiments, thereby obtaining, for each photon-counting spectral computed tomography data set, a corresponding optimized energy bin parameter set, generating GT a plurality of training pairs, each training pair of the plurality of training pairs comprising one photon-counting spectral computed tomography data set of the plurality of photon-counting spectral computed tomography data sets and the corresponding optimized energy bin parameter set, and training TA the machine learning algorithm based on the plurality of training pairs, thereby obtaining a trained machine learning algorithm for providing an optimized energy bin parameter set for photon-counting spectral computed tomography.

If available, manually optimized energy bin parameter sets that have been optimized manually by a user based on photon-counting spectral computed tomography data sets can be used for training of the machine learning algorithm for providing an optimized energy bin parameter set for photon-counting spectral computed tomography. Manually optimized energy bin parameter sets can be used, for example, in addition to or as a substitute to the optimized energy bin parameter sets obtained in step PM. A training pair can therefore comprise one photon-counting spectral computed tomography data set of the plurality of photon-counting spectral computed tomography data sets and the corresponding manually optimized energy bin parameter set.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

BIBLIOGRAPHY

[1] T. Weidinger, T. M. Buzug, T. Flohr, S. Kappler, F. Schöck and K. Stierstorfer, "Threshold optimization for efficient contrast imaging with quantum counting CT detectors", SPIE Medical Imaging 2013, Physics of Medical Imaging.

P. He, B. Wei, W. Cong and G. Wang, "Optimization of K-edge imaging with spectral CT", Med. Phys. 39 (11), 2012.

[3] B. Meng, W. Cong, Y. Xi, B. D. Man and G. Wang, "Energy Window Optimization for X-ray K-edge Tomographic Imaging", IEEE Trans Biomed Eng. 2016 August, 63(8), 1623-1630.

[4] S. J. Nik, J. Meyer and R. Watts, "Optimal material discrimination using spectral x-ray imaging", Phys. Med. Biol. 56 (2011) 5969-5983.

[5] X. Wang, J. Xu and E. C. Frey, "Optimization of energy window widths in basis material decomposition using a multi-window photon counting X-ray detector", IEEE Nuclear Science Symposium Conference Record, 2007.

What is claimed is:

1. A method for providing an optimized energy bin parameter set for photon-counting spectral computed tomography, the method comprising:
receiving photon-counting spectral computed tomography data related to a plurality of energy bins and an initial energy bin parameter set;
performing a plurality of iteration steps,
wherein an input of a first iteration step of the plurality of iteration steps comprises the initial energy bin parameter set as an input energy bin parameter set, and
wherein an input of each further iteration step of the plurality of iteration steps comprises an adjusted energy bin parameter set calculated in a preceding iteration step of the plurality of iteration steps as the input energy bin parameter set; and
providing the optimized energy bin parameter set based on the adjusted energy bin parameter set calculated in a last iteration step of the plurality of iteration steps,
and wherein each iteration step of the plurality of iteration steps comprises:
a) calculating medical image data by applying at least one reconstruction algorithm onto the photon-counting spectral computed tomography data and the input energy bin parameter set,
b) calculating segmentation data related to an anatomical structure in the medical image data by applying at least one segmentation algorithm onto the medical image data,
c) calculating evaluation data by applying an evaluation algorithm onto the segmentation data, and
d) calculating the adjusted energy bin parameter set by applying an optimization algorithm onto the evaluation data and the input energy bin parameter set.

2. The method of claim 1, wherein the optimized energy bin parameter set comprises a plurality of weighting parameters, and wherein the at least one reconstruction algorithm is configured for weighting subsets of the photon-counting spectral computed tomography data relative to other subsets of the photon-counting spectral computed tomography data based on the weighting parameters.

3. The method of claim 2, wherein the segmentation algorithm is a trained deep learning based semantic segmentation algorithm.

4. The method of claim 2, wherein the evaluation algorithm is a trained deep learning based evaluation algorithm.

5. The method of claim 2, wherein each iteration step of the plurality of iteration steps further comprises:
determining, whether a termination criterion is fulfilled based on the evaluation data.

6. The method of claim 2, wherein the optimization algorithm is at least one of an iterative optimization algorithm and an evolutionary optimization algorithm.

7. A method for providing a medical image, the method comprising:
performing the method of claim 2 to obtain the optimized energy bin parameter set;
calculating the medical image by applying a reconstruction algorithm onto the photon-counting spectral computed tomography data and the optimized energy bin parameter set; and
providing the medical image.

8. A method for providing a segmentation of an anatomical structure, the method comprising:
performing the method of claim 2 to obtain the optimized energy bin parameter set;
calculating medical image data by applying at least one reconstruction algorithm onto the photon-counting spectral computed tomography data and the optimized energy bin parameter set;
calculating the segmentation of the anatomical structure in the medical image data by applying at least one segmentation algorithm onto the medical image data; and
providing the segmentation of the anatomical structure.

9. A training method for training a machine learning algorithm for providing an optimized energy bin parameter set for photon-counting spectral computed tomography, the method comprising:
receiving a plurality of photon-counting spectral computed tomography data sets and an initial energy bin parameter set,
performing the method of claim 2 for each photon-counting spectral computed tomography data set of the plurality of photon-counting spectral computed tomography data sets, to obtain, for each photon-counting spectral computed tomography data set, a corresponding optimized energy bin parameter set;
generating a plurality of training pairs, each training pair of the plurality of training pairs comprising one photon-counting spectral computed tomography data set of the plurality of photon-counting spectral computed tomography data sets and the corresponding optimized energy bin parameter set; and
training the machine learning algorithm based on the plurality of training pairs, to obtain a trained machine learning algorithm for providing an optimized energy bin parameter set for photon-counting spectral computed tomography.

10. A non-transitory computer program product storing program elements to induce a providing unit to carry out the method of claim 2, when the program elements are loaded into a memory of the providing unit.

11. A non-transitory computer-readable medium storing program elements, readable and executable by a providing unit, to perform the method of claim 2, when the program elements are executed by the providing unit.

12. The method of claim 1, wherein the segmentation algorithm is a trained deep learning based semantic segmentation algorithm.

13. The method of claim 12, wherein the evaluation algorithm is a trained deep learning based evaluation algorithm.

14. The method of claim 1, wherein the evaluation algorithm is a trained deep learning based evaluation algorithm.

15. The method of claim 1, wherein each iteration step of the plurality of iteration steps further comprises:
 determining, whether a termination criterion is fulfilled based on the evaluation data.

16. A method for providing a medical image, the method comprising:
 performing the method of claim 15 to obtain the optimized energy bin parameter set;
 calculating the medical image by applying a reconstruction algorithm onto the photon-counting spectral computed tomography data and the optimized energy bin parameter set; and
 providing the medical image.

17. A method for providing a segmentation of an anatomical structure, the method comprising:
 performing the method of claim 15 to obtain the optimized energy bin parameter set;
 calculating medical image data by applying at least one reconstruction algorithm onto the photon-counting spectral computed tomography data and the optimized energy bin parameter set;
 calculating the segmentation of the anatomical structure in the medical image data by applying at least one segmentation algorithm onto the medical image data; and
 providing the segmentation of the anatomical structure.

18. A training method for training a machine learning algorithm for providing an optimized energy bin parameter set for photon-counting spectral computed tomography, the method comprising:
 receiving a plurality of photon-counting spectral computed tomography data sets and an initial energy bin parameter set,
 performing the method of claim 15 for each photon-counting spectral computed tomography data set of the plurality of photon-counting spectral computed tomography data sets, to obtain, for each photon-counting spectral computed tomography data set, a corresponding optimized energy bin parameter set;
 generating a plurality of training pairs, each training pair of the plurality of training pairs comprising one photon-counting spectral computed tomography data set of the plurality of photon-counting spectral computed tomography data sets and the corresponding optimized energy bin parameter set; and
 training the machine learning algorithm based on the plurality of training pairs, to obtain a trained machine learning algorithm for providing an optimized energy bin parameter set for photon-counting spectral computed tomography.

19. The method of claim 1, wherein the optimization algorithm is at least one of an iterative optimization algorithm and an evolutionary optimization algorithm.

20. A method for providing a medical image, the method comprising:
 performing the method of claim 1 to obtain the optimized energy bin parameter set;
 calculating the medical image by applying a reconstruction algorithm onto the photon-counting spectral computed tomography data and the optimized energy bin parameter set; and
 providing the medical image.

21. A method for providing a segmentation of an anatomical structure, the method comprising:
 performing the method of claim 1 to obtain the optimized energy bin parameter set;
 calculating medical image data by applying at least one reconstruction algorithm onto the photon-counting spectral computed tomography data and the optimized energy bin parameter set;
 calculating the segmentation of the anatomical structure in the medical image data by applying at least one segmentation algorithm onto the medical image data; and
 providing the segmentation of the anatomical structure.

22. A training method for training a machine learning algorithm for providing an optimized energy bin parameter set for photon-counting spectral computed tomography, the method comprising:
 receiving a plurality of photon-counting spectral computed tomography data sets and an initial energy bin parameter set,
 performing the method of claim 1 for each photon-counting spectral computed tomography data set of the plurality of photon-counting spectral computed tomography data sets, to obtain, for each photon-counting spectral computed tomography data set, a corresponding optimized energy bin parameter set;
 generating a plurality of training pairs, each training pair of the plurality of training pairs comprising one photon-counting spectral computed tomography data set of the plurality of photon-counting spectral computed tomography data sets and the corresponding optimized energy bin parameter set; and
 training the machine learning algorithm based on the plurality of training pairs, to obtain a trained machine learning algorithm for providing an optimized energy bin parameter set for photon-counting spectral computed tomography.

23. A computed tomography device, comprising:
 a detector, configured to acquire photon-counting spectral computed tomography data related to a plurality of energy bins,
 a processor, configured to apply a machine learning algorithm trained by the training method of claim 22 to the photon-counting spectral computed tomography data, thereby obtaining an optimized energy bin parameter set,
 a medical image calculation unit, configured to calculate a medical image by applying a reconstruction algorithm onto the photon-counting spectral computed tomography data and the optimized energy bin parameter set.

24. A non-transitory computer program product storing program elements to induce a providing unit to carry out the method of claim 1, when the program elements are loaded into a memory of the providing unit.

25. A non-transitory computer-readable medium storing program elements, readable and executable by a providing unit, to perform the method of claim 1, when the program elements are executed by the providing unit.

26. A providing unit for providing an optimized energy bin parameter set for photon-counting spectral computed tomography, the providing unit comprising:
 a receiving unit, configured to receive photon-counting spectral computed tomography data related to a plurality of energy bins and an initial energy bin parameter set;
 an iteration unit, configured to perform a plurality of iteration steps,
  wherein an input of a first iteration step of the plurality of iteration steps comprises the initial energy bin parameter set as an input energy bin parameter set, and wherein the input of each further iteration step of the plurality of iteration steps comprises an adjusted energy bin parameter set calculated in a preceding iteration step of the plurality of iteration steps as the input energy bin parameter set; and an energy bin parameter set providing interface, configured to provide the optimized energy bin parameter set based on the adjusted energy bin parameter set calculated in a last iteration step of the plurality of iteration steps, wherein the iteration unit comprises:
- a) a medical image calculation unit, configured to calculate medical image data by applying at least one reconstruction algorithm onto the photon-counting spectral computed tomography data and the input energy bin parameter set,
- b) a segmentation data calculation unit, configured to calculate segmentation data related to an anatomical structure in the medical image data by applying at least one segmentation algorithm onto the medical image data,
- c) an evaluation data calculation unit, configured to calculate evaluation data by applying an evaluation algorithm onto the segmentation data,
- d) an optimization calculation unit configured to calculate the adjusted energy bin parameter set by applying an optimization algorithm onto the evaluation data and the input energy bin parameter set.

27. The providing unit of claim 26, further comprising a medical image providing interface, configured to provide a medical image.

28. The providing unit of claim 26, further comprising a segmentation providing interface, configured to provide a segmentation of an anatomical structure.

* * * * *